United States Patent
Ballez et al.

(10) Patent No.: US 11,464,714 B2
(45) Date of Patent: Oct. 11, 2022

(54) W/O EMULSION FOR IMPREGNATING NONWOVEN FABRIC

(71) Applicant: DR. SCHUMACHER GMBH, Malsfeld (DE)

(72) Inventors: Mike Ballez, Malsfeld (DE); Julia Fuss, Malsfeld (DE); Jens Nielsen, Malsfeld (DE)

(73) Assignee: DR. SCHUMACHER GMBH, Malsfeld (DE)

( * ) Notice: Subject to any disclaimer, the term of this patent is extended or adjusted under 35 U.S.C. 154(b) by 148 days.

(21) Appl. No.: 16/764,652

(22) PCT Filed: Nov. 16, 2018

(86) PCT No.: PCT/DE2018/100937
§ 371 (c)(1),
(2) Date: Jul. 7, 2020

(87) PCT Pub. No.: WO2019/096355
PCT Pub. Date: May 23, 2019

(65) Prior Publication Data
US 2020/0323744 A1  Oct. 15, 2020

(30) Foreign Application Priority Data
Nov. 17, 2017  (DE) .................... 10 2017 127 199.6

(51) Int. Cl.
| | |
|---|---|
| *A61K 8/02* | (2006.01) |
| *A61K 8/06* | (2006.01) |
| *A61K 8/37* | (2006.01) |
| *A61K 8/92* | (2006.01) |
| *A61Q 19/10* | (2006.01) |

(52) U.S. Cl.
CPC ............ *A61K 8/0208* (2013.01); *A61K 8/064* (2013.01); *A61K 8/375* (2013.01); *A61K 8/922* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 2010/0242796 | A1 | 9/2010 | Sorns et al. |
| 2011/0020258 | A1 | 1/2011 | Lorant |
| 2020/0085723 | A1* | 3/2020 | Valverde .................. A61K 8/29 |

FOREIGN PATENT DOCUMENTS

| | | |
|---|---|---|
| EP | 1171094 B1 | 6/2006 |
| EP | 2092929 A1 | 8/2009 |
| EP | 2921159 A1 | 9/2015 |
| WO | 2013/120829 A2 | 8/2013 |

OTHER PUBLICATIONS

Technical Information, ISOLAN GPS: Natural emulsifier for W/O lotions with high formulation flexibility; pp. 1-6, Jun. 2016, Evonik Industries AG.
L. Rigano et al.: Olive Oil—Derived Polyfunctional Vehicles; SOFW-Journal, pp. 20-28; Jun. 2009.
J. Meyer et al.: "A Novel PEG-free Emulsifier Designed for Formulating W/O Lotions with a Light Skin Feel", Nov. 2005, pp. 20-26.
Evonik Industries: Emulsifiers for Skin Care Applications; 2008.
International Search Report issued in International Patent Application No. PCT/DE2018/100937 dated Mar. 11, 2019.

* cited by examiner

*Primary Examiner* — Nannette Holloman
(74) *Attorney, Agent, or Firm* — Fox Rothschild LLP

(57) ABSTRACT

The invention relates to a W/O emulsion for impregnating nonwoven containing 10-60% by weight of vegetable oil, 0.1-25% by weight of emollients, 10 to 50% by weight of water, a lipophilic emulsifier, an inorganic salt as well as at least one antioxidant, wherein the emulsifier is polyglyceryl-4-diisostearate/polyhydroxystearate/sebacate and the viscosity of the emulsion is 250-600 mPa·s, determined using a DIN measuring system 33 according to ISO 53019 at a temperature of 293.15 K and at a rotation speed of 500 r/min.

9 Claims, 2 Drawing Sheets

W/O EMULSION FOR IMPREGNATING NONWOVEN FABRIC

CROSS REFERENCE TO RELATED APPLICATIONS

Figure 1:
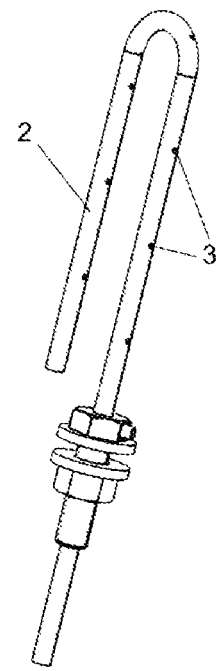

This application is a § 371 national phase entry of International Patent Application No. PCT/DE2018/100937, filed on Nov. 16, 2018, that claims priority to DE 10 2017 127 199.6, filed Nov. 17, 2017, the entireties of which are incorporated herein by reference.

As it is known, wet wipes contain nonwovens which are impregnated with a generally liquid preparation which, among other things, contains a cleaning and/or nourishing ingredient. By now wet wipes are used in many areas of personal care and especially baby care and are very popular as they provide the possibility of a quick and convenient cleaning and care, respectively, without the need for additional water. Usually packaged in handy units of approximately 10 to 100 wipes, wet wipes are also distinguished by their portability and, thanks to this property in particular, cannot be imagined to be missing in our increasingly mobile society.

Usually, the nonwovens contained in wet wipes are impregnated with oil-in-water emulsions (O/W emulsions) in which the oil phase is dispersed in the continuous aqueous phase. However, water-in-oil emulsions (W/O emulsions) in which the oil phase is the continuous phase in which the aqueous phase is dispersed, have a greater care effect than O/W emulsions. Moreover, another advantage of W/O emulsions over O/W emulsions is that active substances contained in the aqueous phase are better protected against oxidation by the surrounding oil phase.

Nonwovens impregnated with a W/O emulsion would therefore be desirable as wet wipes, in particular in order to achieve a greater care effect when using the wet wipes.

However, W/O emulsions are difficult to apply to a nonwoven due to the increased viscosity when compared to O/W emulsions. Furthermore, especially due to the large surface area of wet wipes, there is also an increased difficulty in ensuring the stability of W/O emulsions applied to a nonwoven over a sufficiently long period of time.

Wet wipes known from the prior art therefore contain O/W emulsions as impregnating agents. As an example EP 1 171 094 B1 is mentioned, which describes a wet wipe whose nonwoven is impregnated with an oil-in-water emulsion that contains sterol or a sterol derivative as well as a moisturizer. In addition to water and optionally alcohol, the impregnating agent also contains up to 30% by weight of natural fats or oils.

WO 2013/120829 A1 describes low-viscosity W/O emulsions which contain spreadable oils with oil phases of 10% to 60% and are stabilized by at least two W/O emulsifiers. An impregnation of nonwoven with the W/O emulsions is not described.

US 2011/0020258 A1 describes a low-viscosity W/O emulsion for skin care and for makeup removal, containing a lipophilic emulsifier and a polysaccharide hydrophobized by modification as stabilizers. An impregnation of nonwoven with the W/O emulsion is also not described.

EP 2 921 159 A1 describes a W/O emulsion for removing waterproof make-up, which contains an oil component with a polarity of at least 20 mN/m, water, a lipophilic emulsifier and optionally antioxidants and emollients.

The document "Technical Information ISOLAN GPS", Evonik Nutrition & Care GmbH, describes the suitability of polyglyceryl-4 diisostearate/polyhydroxystearate/sebacate as an emulsifier for W/O emulsions having a low viscosity, which are not suitable, however, to be used as impregnating agents for nonwoven.

OBJECT OF THE INVENTION

It is the object of the present invention to provide an alternative W/O emulsion and an alternative wet wipe, respectively, wherein the W/O emulsion is suitable for impregnating nonwoven and is contained in the wet wipe as an impregnating agent. Therein, the W/O emulsion preferably should be a less expensive impregnating agent than conventional water-free and oil-containing impregnating agents. Preferably, the wet wipe should offer a good cleaning performance and a good care effect, respectively, also with a small amount of impregnation.

GENERAL DESCRIPTION OF THE INVENTION

The invention achieves the object with the features of the claims and in particular with a W/O emulsion for impregnating nonwoven containing or consisting of 10-60% by weight vegetable oil, 0.1-25% by weight of emollients, 10 to 50% by weight of water, a lipophilic emulsifier, an inorganic salt, and at least one antioxidant wherein the emulsifier is polyglyceryl-4-diisostearate/polyhydroxystearate/sebacate. The viscosity of the emulsion preferably is 250-600 mPa·s.

All viscosities determined in connection with the present invention were determined using a rotary rheometer, type R180, DIN measuring system 33 according to ISO 53019 at a temperature of 293.15 K and at a rotation speed of 500 r/min. Accordingly, all viscosity information contained in the present application refer to these measurement parameters.

As already mentioned at the beginning, it is particularly difficult for wet wipes due to their large surface area to ensure the stability of the emulsions used as impregnating agents and thus to provide a long-term stable end product. This applies in particular to W/O emulsions, which naturally have a higher viscosity than O/W emulsions.

While the viscosity of conventional W/O emulsions is, for example, approximately 800 mPa·s, the viscosity of the W/O emulsion according to the invention is only 250-600 mPa·s, for example 300-500 mPa·s or 300-350 mPa·s. According to a preferred embodiment, the viscosity of the W/O emulsion according to the invention is <500 mPa·s, in particular 250-450 mPa·s, and according to a particularly preferred embodiment, the viscosity of the W/O emulsion according to the invention is <450 mPa·s, in particular 250-400 mPa·s or 250-350 mPa·s.

It has surprisingly been found for a person skilled in the art that the low viscosity W/O emulsion according to the invention based on vegetable oil is suitable for use in wet wipes and as impregnant for the nonwoven used in wet wipes, respectively. This is attributed in particular to the high proportion of vegetable oils and to the emulsifier polyglyceryl-4 diisostearate/polyhydroxystearate/sebacate as well as to the ratio of oil phase to emulsifier.

Although the emulsifier contained in the W/O emulsion according to the invention is already known from the document "Technical Information ISOLAN GPS" mentioned above, the formulations disclosed therein containing the emulsifier are not suitable for impregnating nonwoven, since even the two most fluid compositions already have a viscosity of >700 mPa·s or even >900 mPa·s, respectively, (measured using a rotary rheometer, type R180, DIN measuring system 33 according to ISO 53019 at a temperature of 293.15 K and at a rotation speed of 500 r/min) and therefore do not have a sufficiently low viscosity in order to be applied evenly to a nonwoven as an impregnating agent. Furthermore, the emulsions known from this document in addition to the emulsifier polyglyceryl-4-diisostearate/polyhydroxystearate/sebacate still require further stabilizers providing consistency, e.g. microcrystalline wax or zinc stearate, especially in a cold/cold production. In contrast thereto, with the emulsion according to the invention due to the different frame formulation having a particularly high vegetable oil content, no further organic or consistency-providing stabilizer is required and the emulsion according to the invention preferably contains polyglyceryl-4-diisostearate/polyhydroxystearate/sebacate as the sole emulsifier.

The oil content of 10-60% by weight, preferably 20-50% by weight and particularly preferred 25-45% by weight, contained in the W/O emulsion according to the invention can be formed by only one vegetable oil according to one embodiment, or, according to an alternative embodiment, by several different vegetable oils. Preferably, the vegetable oil or vegetable oils, respectively, are selected from the group comprising sunflower oil, rapeseed oil, almond oil, jojoba oil, avocado oil, coconut oil and mixtures of two or more of these oils.

The W/O emulsion according to the invention also contains 0.1-25% by weight, more preferably 5-20% by weight and particularly preferably 10-15% by weight of emollients. For the purposes of the invention, emollients are generally understood to mean compounds which give the skin suppleness, e.g. lipids, especially having a chain length of approximately 14 to 16 carbon atoms.

Optionally, the W/O emulsion according to the invention also contains one ester oil or more ester oils as emollients, the total proportion of oil in the emulsion preferably not exceeding 60% by weight. In particular, isopropyl myristate, isopropyl palmitate and/or isononanoates can be contained as ester oil in the W/O emulsion.

Alternatively or in addition to ester oil or ester oils, respectively, the W/O emulsion according to the invention also contains one or more dialkyl ethers as emollients, in particular dicaprylyl ether.

The emulsifier polyglyceryl-4 diisostearate/polyhydroxystearate/sebacate has the structural formula shown in FIG. 1, in which PHS denotes a polyhydroxystearate residue and IS denotes an isostearate residue:

In contrast to W/O emulsions known from the prior art which contain more than one emulsifier, the W/O emulsion according to the invention preferably contains only the compound polyglyceryl-4 diisostearate/polyhydroxystearate/sebacate as emulsifier.

According to one embodiment, the emulsifier polyglyceryl-4 diisostearate/polyhydroxy-stearate/sebacate is contained in the W/O emulsion in a ratio of 1:10 to 1:20 to the oil phase, more preferably in a ratio of 1:12 to 1:18 to the oil phase, and particularly preferred in a ratio of 1:14 to 1:17 to the oil phase.

According to the invention, the W/O emulsion also contains 10-50% by weight of water, preferably deionized water. Therein, the water phase preferably contains at least one active ingredient, for example glycerol, urea, panthenol, a water-soluble vitamin, e.g. vitamin C, and/or a plant extract, e.g. allantoin and/or aloe vera.

The emulsion according to the invention contains an inorganic salt as stabilizer, especially an alkali salt or alkaline earth salt. Preferred salts are sulfates, particularly sodium sulfate, potassium sulfate, magnesium sulfate or calcium sulfate. According to a preferred embodiment, the inorganic salt is present in the W/O emulsion according to the invention in a ratio from 1:20 to 1:40 to the water phase and especially in a ratio from 1:30 to 1:35 to the water phase.

Another ingredient in the emulsion is an antioxidant. This can be selected, for example, from the group comprising butylhydroxytoluene, rosemary extract, tocopherol acetate and isomers of tocopherol. The emulsion optionally contains several antioxidants, which can also be selected from the aforementioned group. Regardless of whether the W/O emulsion contains one or more antioxidants, the weight proportion of antioxidant preferably is 0.01-0.025% by weight per % by weight of oil phase.

Advantageously, the W/O emulsion according to the invention, in particular due to the water content of up to 50% by weight, is less expensive than conventional water-free impregnants on an oil basis.

The invention also relates to a process for producing a W/O emulsion which contains or consists of
    10-60% by weight of vegetable oil,
    0.1-25% by weight of emollients,
    10-50% by weight of water,
    a lipophilic emulsifier,
    an inorganic salt, and
    at least one antioxidant,
wherein the emulsifier is polyglyceryl-4 diisostearate/polyhydroxystearate/sebacate and the viscosity of the emulsion is 250-600 mPa·s.

In the process according to the invention, an aqueous phase containing water, an inorganic salt and at least one antioxidant as well as optionally at least one active ingredient is added, with stirring, into an oil phase containing the emulsifier polyglyceryl-4 diisostearate/polyhydroxystearate/sebacate.

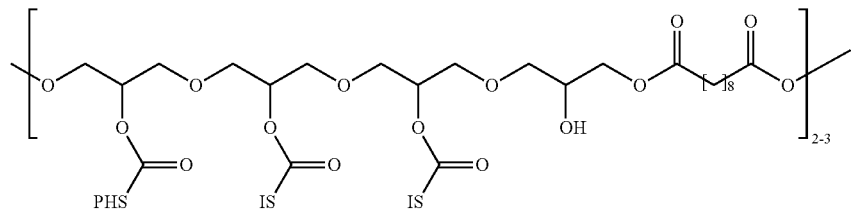

The production of the W/O emulsion, including the stirring of the aqueous phase into the oil phase, preferably is carried out entirely at room temperature, i.e. without heating. This is possible because the emulsion according to the invention does not contain any solid ingredients that need to be liquefied by the application of heat.

Besides, all ingredients used in the process according to the invention, i.e. the vegetable oil, the emollients, the water, the lipophilic emulsifier, the inorganic salt and the at least one antioxidant have the same nature as described above with reference to the W/O emulsion according to the invention. In particular, this also applies to the type of ingredients, e.g. the type of vegetable oil, salt and antioxidant, as well as to their weight percentages.

Optionally, the oil phase used in the process according to the invention in addition to vegetable oil also contains ester oil as an emollient, wherein the total proportion of vegetable oil and ester oil used in the emulsion is max. 60% by weight. In particular, isopropyl myristate, isopropyl palmitate and/or isononanoate can be used as ester oil in the production of the W/O emulsion.

The invention also relates to a wet wipe comprising a nonwoven impregnated with a W/O emulsion according to the invention, i.e. with a W/O-emulsion containing or consisting of

- 10-60% by weight of vegetable oil,
- 0.1-25% by weight of emollients,
- 10-50% by weight of water,
- a lipophilic emulsifier,
- an inorganic salt, and
- at least one antioxidant, wherein the emulsifier is polyglyceryl-4 diisostearate/polyhydroxystearate/sebacate and the viscosity of the emulsion is 250-600 mPa·s.

For production of the wet wipe according to the invention, the W/O-emulsion preferably is applied onto the nonwoven using a special nozzle unit. This comprises a number of outlet tubes, each of which has a number of outlet openings. Therein, the outlet openings are arranged in a depression which is arranged in the longitudinal direction of the outlet tube and extends over a portion of the length of the outlet tube or over its entire length. For example, the depression can be milled into the outlet tubes.

Because the outlet openings are each arranged in a depression arranged in the longitudinal direction of the outlet tubes, the W/O-emulsion emerging from the outlet openings initially collects in this depression and is subsequently applied to the nonwoven in film form in order to impregnate it. Thus, an even impregnation of the nonvowen with the emulsion which is more viscous than O/W-emulsions is possible. An even impregnation by means of a nozzle unit known from the prior art without a respective depression in the region of the outlet openings in which the emulsion could accumulate is not possible due to the higher viscosity of the emulsion, but would merely lead to a point by point or uneven impregnation, respectively.

According to a preferred embodiment, the nozzle unit by means of which the W/O-emulsion is applied to the nonwoven, as is also known from the prior art, comprises a plurality of outlet tubes which, however, have a higher number of outlet openings than is known from the prior art. This increased number of outlet openings serves in particular to fill the depressions arranged in the longitudinal direction of the outlet tubes with emulsion as effectively as possible. Therein, the depression acts as a kind of reservoir for the W/O-emulsion to be applied, with which the nonwoven is contacted for impregnation.

According to one embodiment, the nonwoven contained in the wet wipe according to the invention consists of viscose fibers and/or Lyocell fibers and/or PET fibers, i.e. it can either consist of 100% viscose fibers, Lyocell fibers or PET fibers, or consist of mixed fibers thereof.

Optionally, the nonwoven also contains microfibers and/or cotton fibers, for example in an amount of up to 10% by weight each, in particular from 0.1 to 5.0% by weight.

According to a preferred embodiment, the nonwoven contained in the wet wipe according to the invention consists of viscose fibers and/or lyocell fibers and/or PET fibers and additionally 0.1-5.0% by weight of microfibers and/or 0.1-5.0% by weight cotton fibers.

Particularly preferably, the nonwoven of a wet wipe according to the invention comprises or consists of 30-70% by weight of viscose fibers and 30-70% by weight of PET fibers and optionally 0.1-5.0% by weight of microfibers and/or 0.1-5.0% by weight of cotton fibers.

In embodiments in which the nonwoven contains neither lyocell fibers, nor microfibers or cotton fibers, but exclusively consists of viscose fibers and PET fibers, the proportion of viscose fibers to PET fibers can vary continuously, for example from 1% by weight viscose fibers/99% by weight PET fibers to 99% by weight viscose fibers/1% by weight PET fibers.

Since the impregnant of the wet wipe according to the invention is the W/O-emulsion according to the invention described above, all features disclosed in connection with the specification of the emulsion according to the invention, especially with regard to the ingredients and their proportions by weight, also apply to the W/O emulsion used as impregnant for the wet wipe according to the invention.

In particular due to its low viscosity, compared to known W/O emulsions, of 250-600 mPa·s, preferably 300-500 mPa·s and particularly preferably 300-350 mPa·s, the impregnant applied to a nonwoven in the wet wipe according to the invention is stable, especially stable against oxidation. Therein, the impregnant preferably contains exclusively the emulsifier polyglyceryl-4 diisostearate/polyhydroxystearate/sebacate and no other emulsifier. Furthermore, the impregnant also does not contain any mineral oils.

It has surprisingly been found that wet wipes according to the invention even with a small amount of impregnation, for example of max. 1.0 g impregnant per gram of nonwoven, achieve a particularly good cleaning performance and a particularly good care effect, respectively. In addition, they are also preferably less expensive to produce than water-free, oil-based wet wipes known from the prior art.

Furthermore, the impregnant is suitable for taking up different active ingredients and can contain different active ingredients, respectively. Depending on the nature of the active ingredient contained in the impregnant or the active ingredients contained in the impregnant, the wet wipe according to the invention is suitable, for example, for face and/or body cleansing, as an anti-aging agent, as an anti-pollution agent, as a face mask, for make-up-removal, as toilet paper and/or for baby cleaning and/or caring. Accordingly, the invention also relates to the use of a wet wipe according to the invention for face and/or body cleansing, as an anti-aging agent, as an anti-pollution agent, as a face mask, for make-up-removal, as toilet paper and/or for baby cleaning and/or caring.

DETAILED DESCRIPTION OF THE INVENTION

The invention will now be described in more detail using exemplary embodiments and with reference to the figures, which schematically show in FIG. 1 an outlet tube known from the prior art for applying impregnant onto nonwoven, in FIG. 2 an outlet tube for applying the emulsion onto nonwoven used in a method according to the invention for producing a wet wipe, in FIG. 3 a further outlet tube for applying the emulsion onto nonwoven used in a method according to the invention for producing a wet wipe, and in FIG. 4 a nozzle unit used in a method according to the invention for producing a wet wipe.

First, the preparation of W/O-emulsions according to the invention is described by means of the following two examples, each of which contains a frame formulation for W/O-emulsions according to the invention. The weight proportions of the individual ingredients in the emulsions can vary within the specified range each time.

EXAMPLE 1: PREPARATION OF A W/O-EMULSION ACCORDING TO THE INVENTION ON THE BASIS OF Rapeseed Oil Table 1 contains a frame formulation for a W/O-emulsion according to the invention based on rapeseed oil.

All ingredients labeled "Phase A" are components of the aqueous phase, all ingredients labeled "Phase B" are components of the oil phase.

TABLE 1

Frame formulation of a W/O-emulsion based on rapeseed oil

| Ingredients | Concentration (% by weight) | Phase |
| --- | --- | --- |
| Water | Ad 100.00 | A |
| Rapeseed Oil | 25.00-50.00 | B |
| Rosemary extract | 0.01-0.10 | B |
| Magnesium sulfate | 1.50 | A |
| Polyglyceryl-4-diisostearate/ polyhydroxystearate/sebacate | 1.50-3.00 | B |
| Glycerin | 1.00-5.00 | A |
| Citric acid | 0.20 | A |
| Sodium benzoate | 0.50 | A |
| Perfume | 0.01-0.40 | B |

For the preparation of the aqueous phase, at first the required amount of water is placed in a vessel at room temperature. Subsequently, magnesium sulfate, glycerin, citric acid and sodium benzoate are added also at room temperature and it is stirred until a clear solution is obtained.

For the preparation of the oil phase, rapeseed oil is placed in a second vessel at room temperature. Now, rosemary extract, the emulsifier polyglyceryl-4-diisostearate/polyhydroxystearate/sebacate and perfume are added and it is stirred until a clear oil phase is obtained.

Subsequently, the aqueous phase is added to the oil phase under vigorous stirring and homogenization, whereby the W/O-emulsion according to the invention is obtained.

The viscosity of the obtained W/O-emulsion according to the frame formulation given in Table 1 is 350-500 mPa·s (determined using DIN measuring system 33 according to ISO 53019 at a temperature of 293.15 K and at a rotation speed of 500 r/min), wherein the viscosity can be influenced within this frame by the intensity of the homogenization. Therein, brief homogenization leads to viscosities in the lower range of the specified frame, and longer homogenization leads to viscosities in the upper range of the specified frame.

EXAMPLE 2: PREPARATION OF A W/O-EMULSION ACCORDING TO THE INVENTION ON THE BASIS OF SUNFLOWER OIL

Table 2 contains a frame formulation for a W/O-emulsion according to the invention based on sunflower oil.

All ingredients labeled "Phase A" are components of the aqueous phase, all ingredients labeled "Phase B" are components of the oil phase.

TABLE 2

Frame formulation of a W/O-emulsion based on sunflower oil

| Ingredients | Concentration (% by weight) | Phase |
| --- | --- | --- |
| Water | Ad 100.00 | A |
| Sunflower Oil | 15.00-30.00 | B |
| Rosemary extract | 0.01-0.10 | B |
| Magnesium sulfate | 0.25-0.75 | A |
| Polyglyceryl-4-diisostearate/ polyhydroxystearate/sebacate | 0.75-2.00 | B |
| Ethylhexyl stearate | 5.00-10.00 | B |
| Glycerin | 1.00-5.00 | A |
| Isopropyl myristate | 5.00-10.00 | B |
| Citric acid | 0.15 | A |
| Almond oil | 0.5-5.0 | B |
| Sodium benzoate | 0.50 | A |
| Perfume | 0.01-0.40 | B |

For the preparation of the aqueous phase, at first the required amount of water is placed in a vessel at room temperature. Subsequently, magnesium sulfate, glycerin, citric acid and sodium benzoate are added also at room temperature and it is stirred until a clear solution is obtained.

For the preparation of the oil phase, sunflower oil is placed in a second vessel at room temperature. Now, rosemary extract, the emulsifier polyglyceryl-4-diisostearate/polyhydroxystearate/sebacate, ethylhexyl stearate, isopropyl myristate, almond oil and perfume are added and it is stirred until a clear oil phase is obtained.

Subsequently, the aqueous phase is added to the oil phase under vigorous stirring and homogenization, whereby the W/O-emulsion according to the invention is obtained.

The viscosity of the obtained W/O emulsion according to the frame formulation given in Table 2 is 330-400 mPa·s (determined using DIN measuring system 33 according to ISO 53019 at a temperature of 293.15 K and at a rotation speed of 500 r/min), wherein the viscosity can be influenced within this frame by the intensity of the homogenization. Therein, brief homogenization leads to viscosities in the lower range of the specified frame, and longer homogenization leads to viscosities in the upper range of the specified frame.

EXAMPLE 3: PREPARATION OF A FURTHER W/O-EMULSION ACCORDING TO THE INVENTION ON THE BASIS OF RAPESEED OIL

Table 3 contains a frame formulation for a W/O-emulsion according to the invention based on rapeseed oil.

All ingredients labeled "Phase A" are components of the aqueous phase, all ingredients labeled "Phase B" are components of the oil phase.

TABLE 3

Frame formulation of a W/O-emulsion based on rapeseed oil

| Ingredients | Concentration (% by weight) | Phase |
| --- | --- | --- |
| Water | Ad 100.00 | A |
| Rapeseed Oil | 15.00-30.00 | B |
| Rosemary extract | 0.01-0.10 | B |
| Magnesium sulfate | 0.25-0.75 | A |
| Polyglyceryl-4-diisostearate/ polyhydroxystearate/sebacate | 0.75-2.00 | B |
| Ethylhexyl stearate | 5.00-10.00 | B |
| Glycerin | 1.00-5.00 | A |
| Dicaprylyl ether | 5.00-10.00 | B |
| Citric acid | 0.15 | A |
| Coconut oil | 0.25-5.00 | B |
| Sodium benzoate | 0.50 | A |
| Perfume | 0.01-0.40 | B |
| Olive oil | 0.25-5.00 | B |

For the preparation of the aqueous phase, the required amount of water is first placed in a vessel at room temperature. Subsequently, magnesium sulfate, glycerin, citric acid and sodium benzoate are added also at room temperature and it is stirred until a clear solution is obtained.

For the preparation of the oil phase, rapeseed oil is placed in a second vessel at room temperature. Now, rosemary extract, the emulsifier polyglyceryl-4-diisostearate/polyhydroxy-stearate/sebacate, ethylhexyl stearate, dicaprylyl ether, coconut oil, olive oil and perfume are added and it is stirred until a clear oil phase is obtained.

Subsequently, the aqueous phase is added to the oil phase under vigorous stirring and homogenization, whereby the W/O-emulsion according to the invention is obtained.

The viscosity of the obtained W/O emulsion according to the frame formulation given in Table 3 is 250-400 mPa·s (determined using DIN measuring system 33 according to ISO 53019 at a temperature of 293.15 K and at a rotation speed of 500 r/min), wherein the viscosity can be influenced within this frame by the intensity of the homogenization. Therein, brief homogenization leads to viscosities in the lower range of the specified frame, and longer homogenization leads to viscosities in the upper range of the specified frame.

FIG. 1 shows an outlet tube 2 for applying impregnant to nonwoven which is known from the prior art. In the depicted embodiment, the outlet tube 2 is curved and has outlet openings 3 distributed over its entire length, through which impregnant, which according to the prior art is usually an O/W-emulsion, can be applied uniformly onto nonwoven.

W/O-emulsions according to the invention, e.g. prepared according to Example 1 or Example 2, have a higher viscosity than O/W emulsions. If one would attempt to apply an emulsion according to the invention onto nonwoven in the way known from the prior art by means of the outlet tubes 2 shown in FIG. 1, this would lead to an uneven or selective impregnation of the nonwoven, respectively, due to the higher viscosity.

Figure 2:
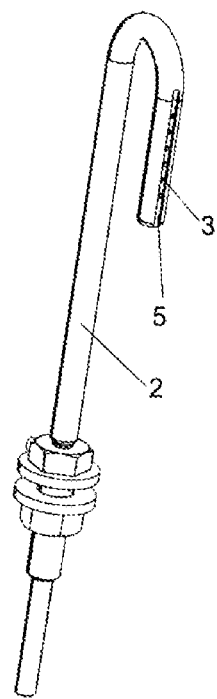
Figure 3:
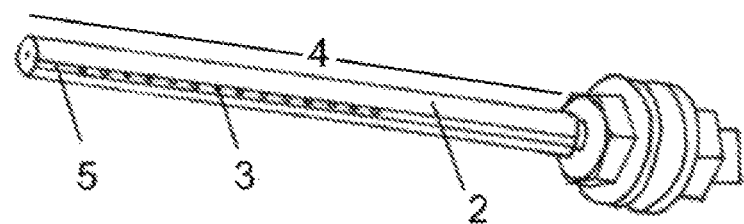
Figure 4:
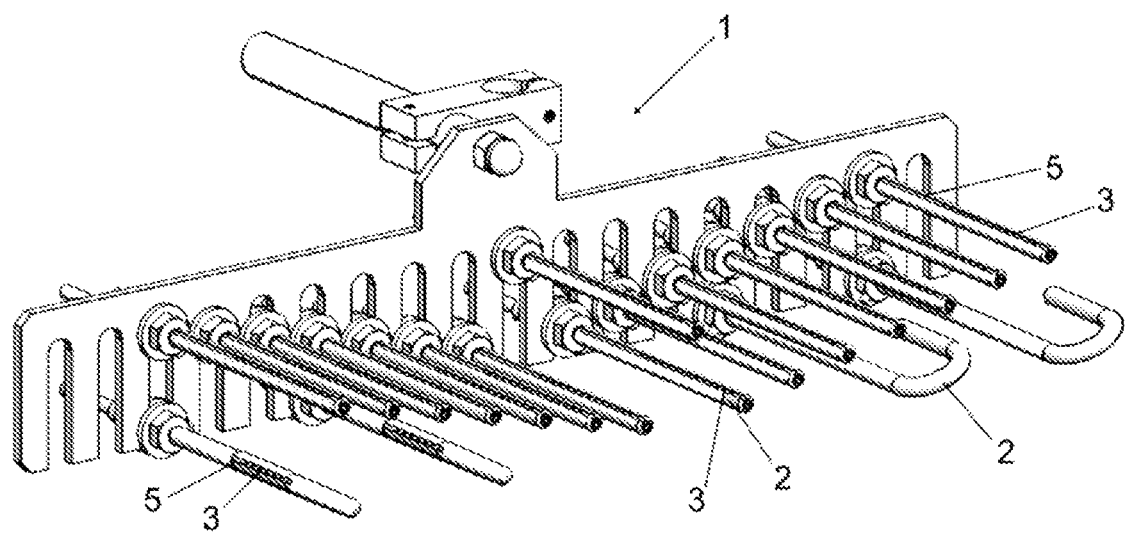

Therefore, the nozzle unit 1 shown schematically in FIG. 4, having several of the curved outlet tubes 2 shown in FIG. 2 and several of the straight outlet tubes 2 shown in FIG. 3 is used for production of wet wipes according to the invention impregnated with W/O-emulsion. Therein, both the curved outlet tubes 2 and the straight outlet tubes 2 have outlet openings 3 which are arranged in an, e.g. milled, depression 5 extending in a longitudinal direction of the outlet tubes 2. The depression 5 having the outlet openings 3 arranged therein can extend over the entire length 4 of the outlet tubes 2 (as depicted in FIG. 3) or only over a portion of their length (as shown in FIG. 2). Preferably, the outlet tubes 2 have outlet openings 2 arranged only in the depression 5, such that the W/O-emulsion emerging from the outlet openings 2 directly comes into the depression 5. In this way, when emulsion emerges through the outlet openings 3, the depression 5 fills like a liquid reservoir and can be applied uniformly to the nonwoven upon contacting.

The features of the invention disclosed in the above description and in the claims may be essential both individually and in any combination for the realization of the invention in its various embodiments.

The invention claimed is:

1. A W/O emulsion for impregnating nonwoven containing
   10-60% by weight of vegetable oil,
   0.1-25% by weight of emollients,
   10 to 50% by weight of water,
   a lipophilic emulsifier,
   an inorganic salt,
   at least one antioxidant,
   wherein the emulsifier is polyglyceryl-4-diisostearate/poly-hydroxystearate/sebacate and the viscosity of the emulsion is 250-600 mPa·s, determined using a DIN measuring system 33 according to ISO 53019 at a temperature of 293.15 K and at a rotation speed of 500 r/min, and wherein the emulsifier polyglyceryl-4-diisostearate/poly-hydroxystearate/sebacate is contained in the W/O emulsion in a ratio of 1:10 to 1:20 to the oil phase.

2. The W/O-emulsion according to claim 1, wherein the vegetable oil is selected from the group comprising sunflower oil, rapeseed oil, almond oil, jojoba oil, avocado oil, coconut oil and mixtures thereof.

3. The W/O-emulsion according to claim 1, wherein the emollients contain ester oil and/or dialkyl ether.

4. The W/O-emulsion according to claim 1, wherein the proportion by weight of antioxidant is 0.01-0.025% by weight per % by weight of oil phase.

5. A process for production of a W/O-emulsion according to claim 1, wherein an aqueous phase containing water, an inorganic salt and at least one antioxidant, is given into an oil phase with stirring, wherein the oil phase contains the emulsifier polyglyceryl-4 diisostearate/polyhydroxystearate/sebacate.

6. The process according to claim 5, wherein the preparation of the W/O-emulsion takes place entirely at room temperature.

7. A wet wipe comprising a nonwoven, wherein the nonwoven is impregnated with a W/O-emulsion according to claim 1.

8. A process for production of a wet wipe according to claim 7, wherein the W/O-emulsion is applied onto the nonwoven by means of a nozzle unit (1) having a plurality of outlet tubes (2), wherein each outlet tube (2) has a plurality of outlet openings (3), arranged in a depression (5) arranged in longitudinal direction of the outlet tube (2) and extending over at least a portion of the length (4) of the outlet tube (2).

9. The process according to claim 8, wherein the W/O-emulsion upon emerging from the outlet openings (3) arranged in the outlet tubes (2) initially accumulates in the depression (5) and subsequently is applied to the nonwoven.

* * * * *